United States Patent [19]
Lee

[11] Patent Number: 5,813,856
[45] Date of Patent: Sep. 29, 1998

[54] DENTAL SUCTION MIRROR

[76] Inventor: Wangkun Lee, Kuk-dong Apt. 101-1802, Hakjang-dong, Sasang-ku, Pusan, Rep. of Korea

[21] Appl. No.: 792,490

[22] Filed: Jan. 31, 1997

[51] Int. Cl.⁶ .................................................. A61C 1/00
[52] U.S. Cl. ............................................. 433/31; 433/91
[58] Field of Search ................................ 433/31, 30, 91, 433/93

[56] References Cited

U.S. PATENT DOCUMENTS

| | | | |
|---|---|---|---|
| 1,660,870 | 2/1928 | Fust | 433/31 |
| 3,924,333 | 12/1975 | Erickson | 433/93 |
| 4,883,426 | 11/1989 | Ferrer | 433/91 |
| 4,906,188 | 3/1990 | Moseley | 433/93 |
| 5,281,134 | 1/1994 | Schultz | 433/31 |

*Primary Examiner*—John J. Wilson
*Attorney, Agent, or Firm*—Notaro & Michalos P.C.

[57] ABSTRACT

A dental suction mirror has a stainless reflecting plate with a slant depression and an oblong groove 13. Three holes having different paths in the inner center and on both sides of the plate connect the groove to the depression. A stainless connection tube having an expanding portion in the form portion thereof and a projecting tube in the rear portion thereof; and a handle tube having an insertion groove along the upper part thereof are connected to the plate. An optical fiber is in the insertion groove, stickers being applied to the groove so as to prevent the optical fiber from leaving the groove. A plastic clip over a narrow portion of the stainless tube curves the optical fiber upwardly over a polished specular surface, and the stainless reflecting plate, the stainless connection tube and the handle tube are coated with nickel-chrome and additionally $SiO_2$.

2 Claims, 5 Drawing Sheets

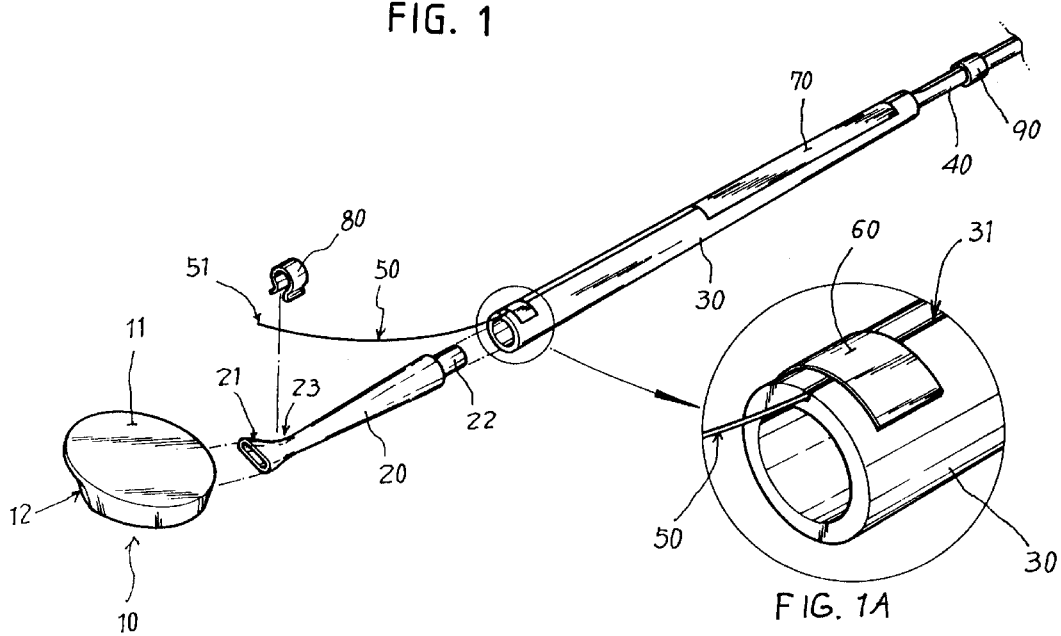
FIG. 1
FIG. 1A
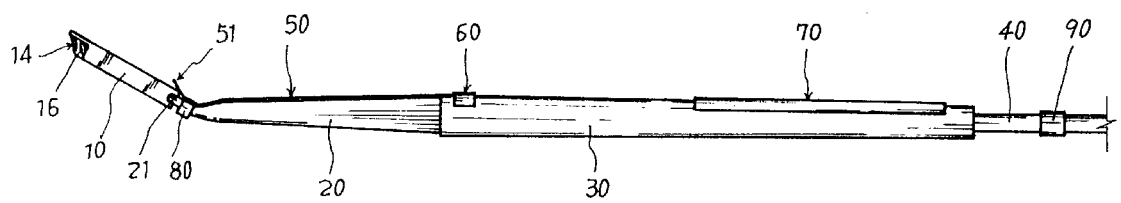
FIG. 2

DENTAL SUCTION MIRROR

BACKGROUND OF THE INVENTION

1. Field of the Invention

The present invention relates to a dental suction mirror and, more particularly, to a dental suction mirror which functions to efficiently suck blood, saliva, cleaning water and antiseptic solution as well as scrapes, the mirror having an optical fiber to brighten the inside of the patient's mouth, a slant surface to prevent the decrease of its suction efficiently and prevent the skin of the mouth from being sucked into the holes thereof, and a stainless connection tube for economical sterilization and replacement.

2. Discussion of Related Art

When a dentist gives a patient a dental treatment such as extracting a tooth, there is inevitable discharged into the mouth, a lot of blood and saliva. The blood and saliva standing in the patient's mouth hinders the dentist in his dental treatment. To allow the dentist to check the teeth and gums of the patient, a suction mirror can be used during a dental treatment.

With this, however, the dentist cannot hold a suction hose for sucking in sand discharging blood, saliva, cleaning water or antiseptic solution standing in the patients mouth, because he has to hold the suction mirror with one hand and a dental tool with the other hand. For this reason, at least one practical nurse to assist the dentist is needed for discharging the blood and saliva from the patient's mouth, using the suction hose.

Therefore, there are caused a lot of problems as follows. If the nurse does not work hand in hand with the dentist in discharging the blood, saliva, cleaning water and antiseptic solution standing in the patient's mouth, a successful treatment for the patient is hard to attain due to undesired blood and saliva in the patient's mouth and a longer time required for the treatment.

Furthermore, the nurse can make mistakes in assisting the dentist and spoil the patient's clothing with the blood and saliva flowing out of the patient's mouth, because it is difficult for the nurse to place the suction hose in an adequate position in the patient's mouth when the dentist, looking into the mouth, obstructs the nurse's view into the mouth.

In addition to the problems as described above, the space for the dental treatment in the patient's mouth gets relatively smaller due to the suction mirror, dental tool sand the suction hose introduced in the mouth during treatment. The patient also suffers, having to reluctantly open this mouth much wider in front of the dentist for a long time.

FIGS. 8, 9 and 10 illustrate a conventional suction mirror to solve the above problems. In the suction mirror, as shown in FIG. 8, a disklike stainless reflecting plate 100 having a polished specular surface 101 is welded to a handle tube 109. In the rear part of the handle tube 109, a screw tube 110 is provided to be inserted into a suction hose 200.

Inside the stainless reflecting plate 100, there are provided a hold 102 piercing to the handle tube 109 and an aperture 105 extending perpendicularly to the hole and in the center of the hole 102. On both sides of the hole 102, holes 103 and 104 are further formed, and slant toward the central aperture 105. The respective three holes 102, 103, 104 have perpendicular apertures 106, 107 and 108, formed near outer ends of the holes.

This known dental suction mirror also has some problems, however, in that the sucked materials are caught in the complex structure where the two bilateral holes 103 and 104 meet at the point of the central aperture 105 formed on the hole 102 piercing the handle tube 109. Dental calculus, tooth pieces and plaster fragments (which is used in a dental pretreatment) are hard to discharge through the handle tube 109 of the conventional suction mirror, because they are sucked through the three holes 102, 103 and 104 and the four aperture 105 through 108, and gather at the edge of the central aperture 105.

Due to the poor suction performance in the prior art, it is required to frequently disconnect the suction hose 200 from the handle tube 109 so as to open the clogged holes, which takes too much time.

Moreover, because the holes 102, 103 and 104 are perpendicular to the outer edge of the stainless reflecting plate 100, and this edge often comes into contact with the skin in the patient's mouth, this lowers the suction efficiency of the suction mirror.

The conventional dental suction mirror whole surface is coated with nickel-chrome is not good for the patient's health. It has no light for brightening the inside of the patient's mouth, which results in difficulty against a precise treatment for the patient.

The suction mirror of the prior art additionally exhibits the disadvantages in that the handle tube 109 has to inconveniently be taken off from the suction hose 200 every time for sterilization and the suction power is weakened due to too many holes formed thereon. Moreover, it is required to replace the whole apparatus when a new suction mirror is to be used.

SUMMARY OF THE INVENTION

Accordingly, the present invention is directed to a dental suction mirror that substantially obviates one or more of the problems due to limitations and disadvantages of the related art.

An object of the present invention is to provide a dental suction mirror, which is to efficiently suck blood, saliva, cleaning water and antiseptic solution as well as scraps, having an optical fiber to brighten the inside of the patient's mouth, a slant surface to prevent a decrease of its suction efficiency and prevent the skin of the mouth from being sucked into the holes thereof, and a stainless connection tube for economical sterilization and replacement.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a dental suction mirror comprising: a stainless reflecting place having a slant depression in the front portion thereof, an oblong groove in the rear portion thereof and three holes having different paths in the inner center and an both sides thereof; a stainless connection tube having an expanding portion in the front portion thereof and a projecting tube in the rear portion thereof; and a handle tube having an insertion groove along the upper part thereof so as to connect the stainless reflecting plate and the stainless connection tube, an optical fiber being inserted into the insertion groove, stickers being applied to the groove so as to prevent the optical fiber from getting out of the groove, a plastic clip being inserted into a narrow portion of the stainless tube so as to fix the optical fiber to curve slightly upwardly over a polished specular surface, and the stainless reflecting plate, the stainless connection tube and the handle tube being coated with nickel-chrome and additionally $SiO_2$.

It is to be understood that both the foregoing general description and the following detailed description are exemplary and explanatory and are intended to provide further explanation of the invention as claimed.

BRIEF DESCRIPTION OF THE DRAWINGS

The accompanying drawing, which are included to provide a further understanding of the invention and are incorporated in and constitute a part of this specification, illustrate embodiments of the invention and together with the description serve to explain the principles of the invention;

In the drawings:

FIG. 1 is a fragmentary perspective view of the present invention;

FIG. 1A is an enlarged detail from the circled area of FIG. 1;

FIG. 2 is a front view of the present invention;

DETAILED DESCRIPTION OF THE PREFERRED EMBODIMENT

Reference will now be made in detail to the preferred embodiments of the present invention, examples of which are illustrated in the accompanying drawings.

Referring to FIGS. 3–7 in the present invention, holes 14, 15, and 16 piercing the inside of a stainless reflecting plate 10 form different paths through the stainless reflecting plate 10 without meeting together at the centering point in the plate. Therefore, the scraps passing through the holes can be successfully discharged through a stainless connection tube 20 and a handle tube 30 shown in FIGS. 1–3, without gathering, which saves the time required to clear the holes of the prior art.

Figure 7:
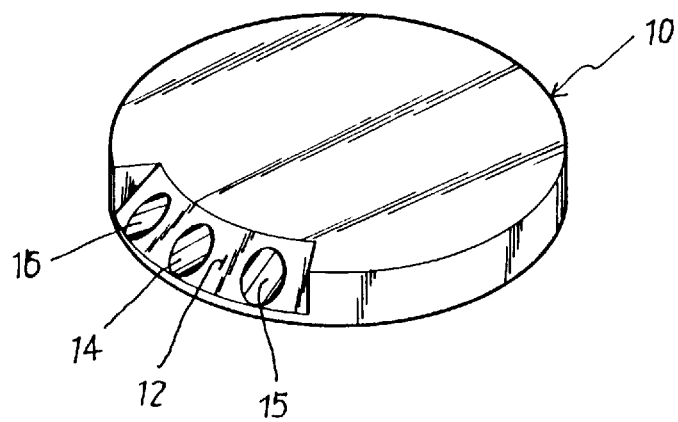
FIG. 7 is a perspective view showing the bottom surface of the stainless reflecting plate in accordance with the present invention.
Figure 8:
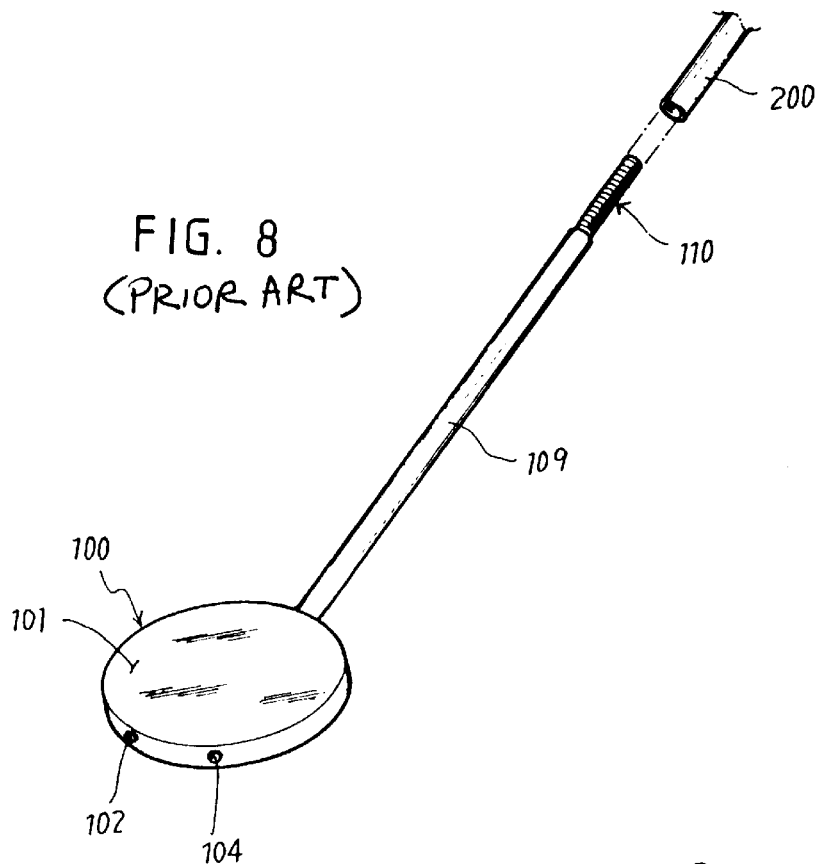
FIG. 8 is a perspective view of the conventional suction mirror.
Figure 9:
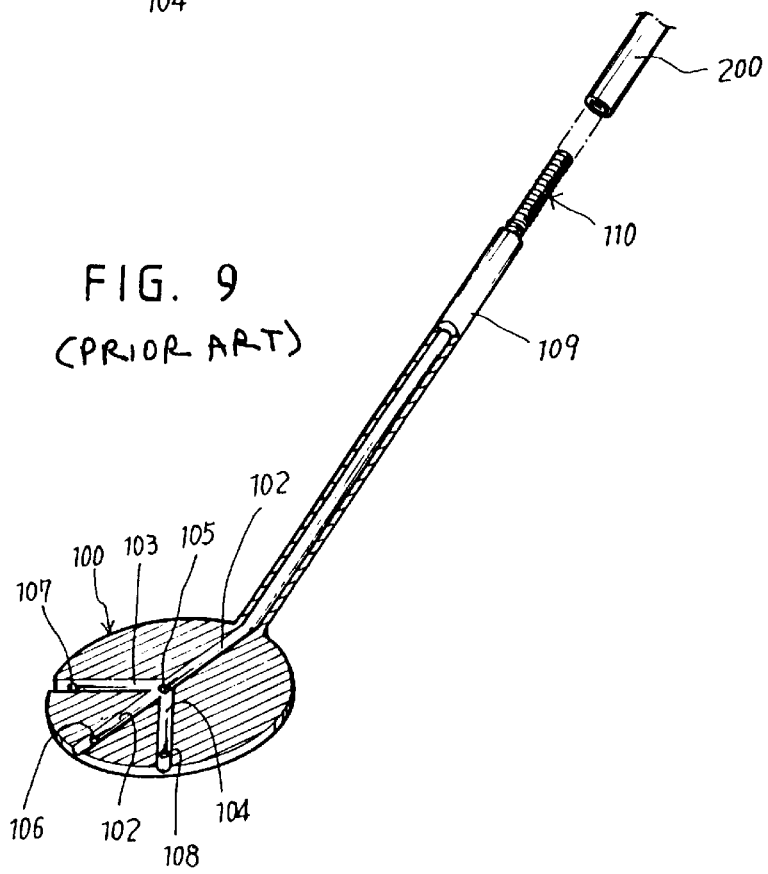
FIGS. 9 and 10 are view showing the construction of the conventional suction mirror.
Figure 10:
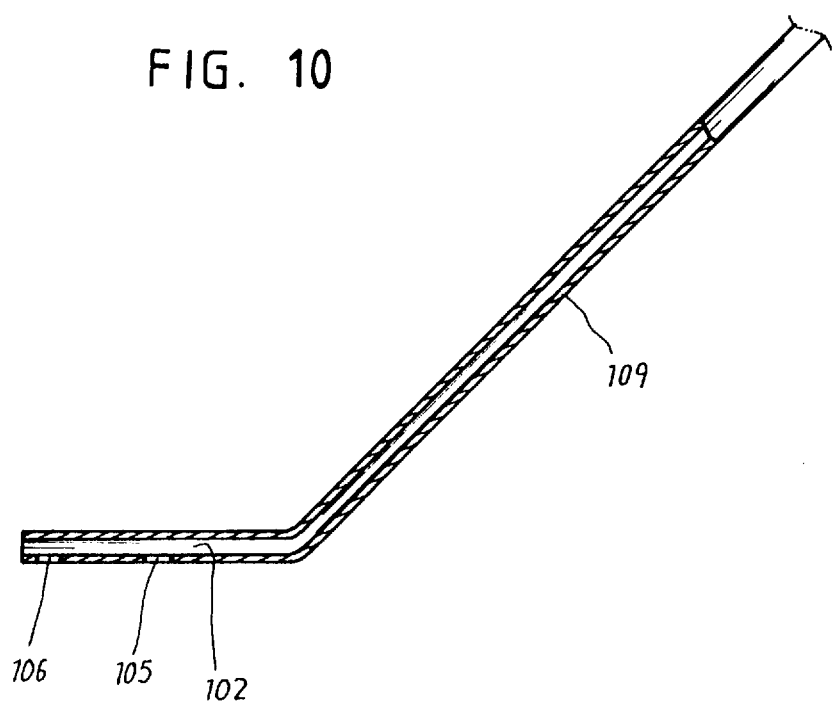

The area of the outer end portions of the holes which contact the skin of a patient's mouth is small because a slant depression 12 is made in the front side of the stainless plate 10 as shown in FIG. 7 and the holes pierce the depression. This solves the problem of the prior art that the skin of the mouth is sucked into the holes during suction.

Additionally, the suction efficiency can be secured because the outer end portions of the holes are spaced apart from the skin inside the patient's mouth as the diameters of the holes get larger in an oblong form due to the slant depression 12. These large holes are also useful for sucking and discharging longer scraps in the mouth under dental treatment.

The present invention is also effective in maintaining the suction efficiency to rapidly discharge blood, saliva, cleaning water and antiseptic solution owing to the small number of the holes provided in the suction mirror.

Figure 3:
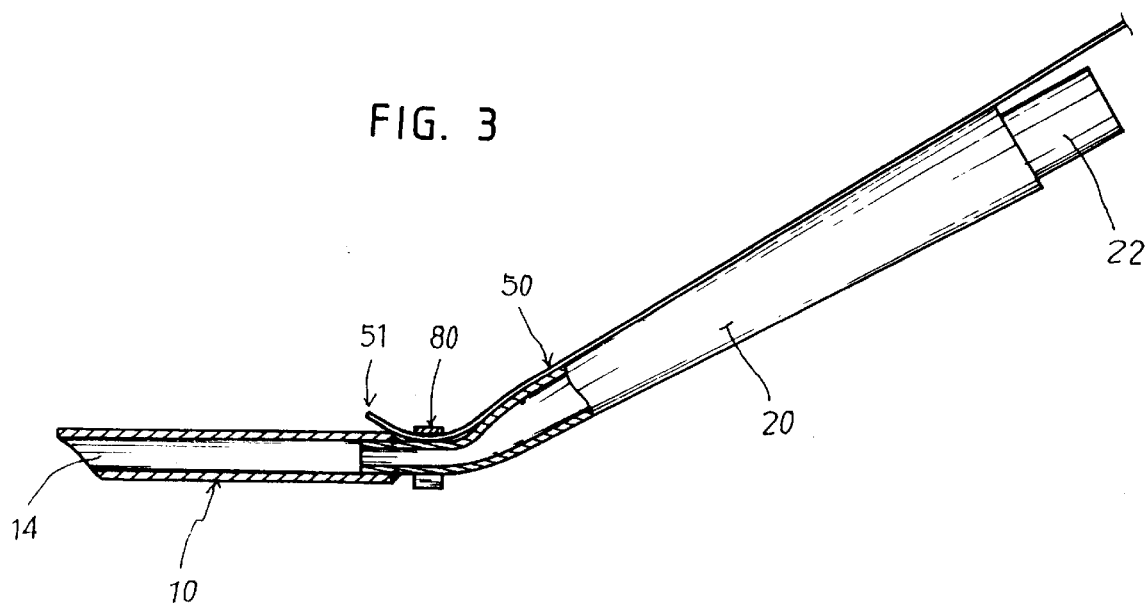
FIG. 3 is a partial expanded sectional view of the present invention.
Figure 4:
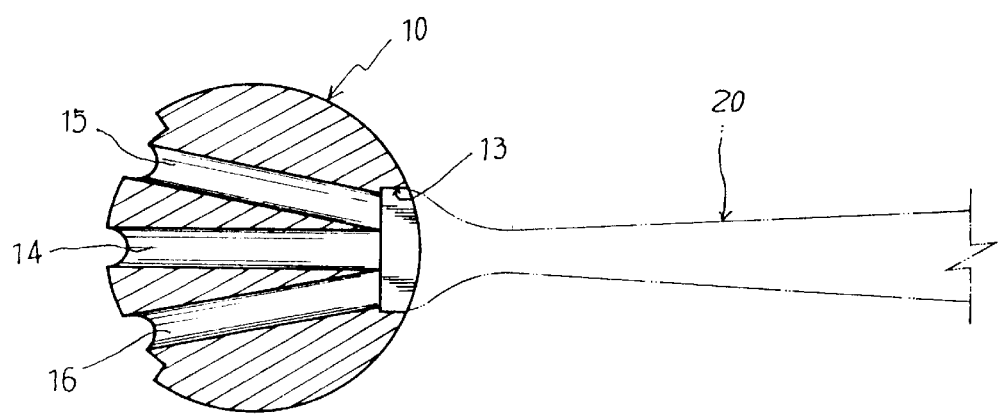
FIG. 4 is a cross-sectional view showing the internal construction of the stainless reflecting plate in accordance with the present invention.
Figure 5:
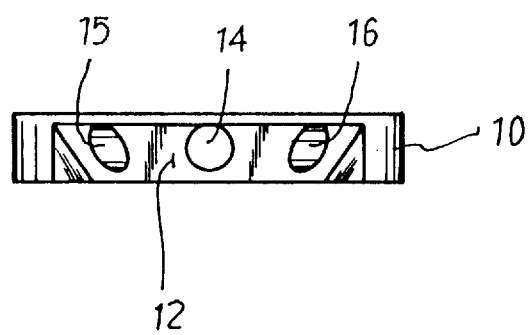
FIGS. 5 and 6 are left and right side views of the stainless reflecting plate in accordance with the present invention.
Figure 6:
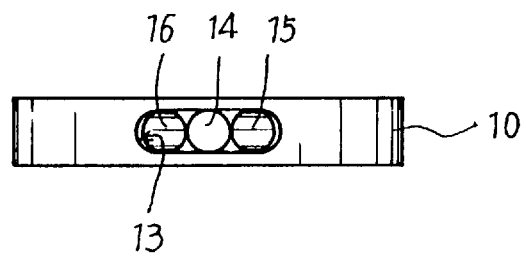

The stainless connection tube 20 is inserted between the stainless reflecting plate 10 and handle tube 30. Thus, it is convenient for sterilization of the stainless reflecting plate 10 and the stainless connection tube 30 by simply taking the stainless connection tube 20 off the handle tube 30 after separating the plastic clip 80. Economically, the handle tube 30 need not be sterilized. Oblong end part 21 of the tube 20, plugs into an oblong groove 13 in the near end of the plate 10 as shown in FIG. 4.

An optical fiber 50 is inserted into an optical fiber's insertion groove 31 of the handle tube 30 and an optical fiber's end portion 51 is made to be curved slightly upwards over a polished specular surface 11. Because the plastic clip 80 is inserted into a narrow part 23 of the stainless connection tube 20, the optical fiber's end portion 51 is curved slightly upwards. Thus, the optical fiber's end portion 51 under the light emitted by a luminous body brightens the dark inside of the patient's mouth. Stickers 60 and 70 hold fiber 50 in groove 31 along handle 30.

In FIG. 2, the rear part of the optical fiber is desirably affixed to a suction hose with a plastic ring 90, more preferably, with several plastic rings. If necessary, it is preferable to use a vinyl tape.

According to the invention, there is no harm to the patient's health because all components are coated with nickel-chrome and additionally with $SiO_2$. When a new device is to be used, economically we have only to replace the stainless plate 10 and the stainless connection tube 20. Further, a thin mirror can be provided on the upper surface of the stainless reflecting plate 10.

It will be apparent to those skilled in the art that various modifications and variations can be made in the dental suction mirror of the present invention without departing from the spirit or scope of the invention. Thus, it is intended that the present invention cover the modifications and variations of this invention provided they come within the scope of the appended claims and their equivalents.

What is claimed is:

1. A dental suction mirror comprising:

a stainless reflecting plate having a slant depression in a front portion thereof, an oblong groove in a rear portion thereof and three holes having different paths in the inner center and on both sides of the plate, the holes connecting the oblong groove to the slant depression;

a stainless connection tube having an expanding front portion connected into the oblong groove and a projecting rear tube; and a handle tube having an insertion groove along an upper part thereof for receiving an optical fiber, the handle tube being connected to the rear tube of the stainless connection tube, an optical fiber in the insertion groove, stickers applied over to the insertion groove to retain the optical fiber over a polished specular surface of the plate; and the stainless reflecting plate, the stainless connection tube and handle the tube being coated with nickel-chrome and additionally $SiO_2$.

2. The dental suction mirror as defined in claim 1, wherein the stainless reflecting plate is provided with a thin mirror on the upper surface thereof.

* * * * *